US012569231B2

(12) United States Patent
Kopel et al.

(10) Patent No.: US 12,569,231 B2
(45) Date of Patent: Mar. 10, 2026

(54) SYSTEM FOR FLUOROSCOPIC TRACKING OF A CATHETER TO UPDATE THE RELATIVE POSITION OF A TARGET AND THE CATHETER IN A 3D MODEL OF A LUMINAL NETWORK

(71) Applicant: Covidien LP, Mansfield, MA (US)

(72) Inventors: Evgeni Kopel, Barkan (IL); Michael E. Calcutt, Burnsville, MN (US); Oren P. Weingarten, Hod-Hasharon (IL)

(73) Assignee: Covidien LP, Mansfield, MA (US)

( * ) Notice: Subject to any disclaimer, the term of this patent is extended or adjusted under 35 U.S.C. 154(b) by 99 days.

(21) Appl. No.: 18/434,241

(22) Filed: Feb. 6, 2024

(65) Prior Publication Data

US 2024/0215963 A1      Jul. 4, 2024

Related U.S. Application Data

(62) Division of application No. 16/742,141, filed on Jan. 14, 2020, now Pat. No. 11,925,333.

(60) Provisional application No. 62/799,822, filed on Feb. 1, 2019.

(51) Int. Cl.
| | |
|---|---|
| *A61B 10/04* | (2006.01) |
| *A61B 5/06* | (2006.01) |
| *A61B 6/00* | (2006.01) |
| *A61B 6/12* | (2006.01) |
| *A61B 6/03* | (2006.01) |
| *A61M 25/01* | (2006.01) |

(52) U.S. Cl.
CPC .............. *A61B 10/04* (2013.01); *A61B 5/062* (2013.01); *A61B 6/12* (2013.01); *A61B 6/487* (2013.01); *A61B 6/032* (2013.01); *A61M 2025/0166* (2013.01)

(58) Field of Classification Search
None
See application file for complete search history.

(56) References Cited

U.S. PATENT DOCUMENTS

2017/0035380 A1* 2/2017 Barak ................... A61B 6/466

* cited by examiner

*Primary Examiner* — Patricia J Park
(74) *Attorney, Agent, or Firm* — Weber Rosselli & Cannon LLP

(57) ABSTRACT

A system and method for confirming placement of a biopsy tool in a target including a navigation component to track the position of a catheter navigated into a luminal network, and a catheter configured to receive a biopsy tool. The system and method receive a first plurality of fluoroscopic images, generate a first fluoroscopic three-dimensional reconstruction from the plurality of fluoroscopic images, and present a first slice of the 3D reconstruction depicting the catheter in relation to a target visible in the slice of the 3D reconstruction.

20 Claims, 7 Drawing Sheets

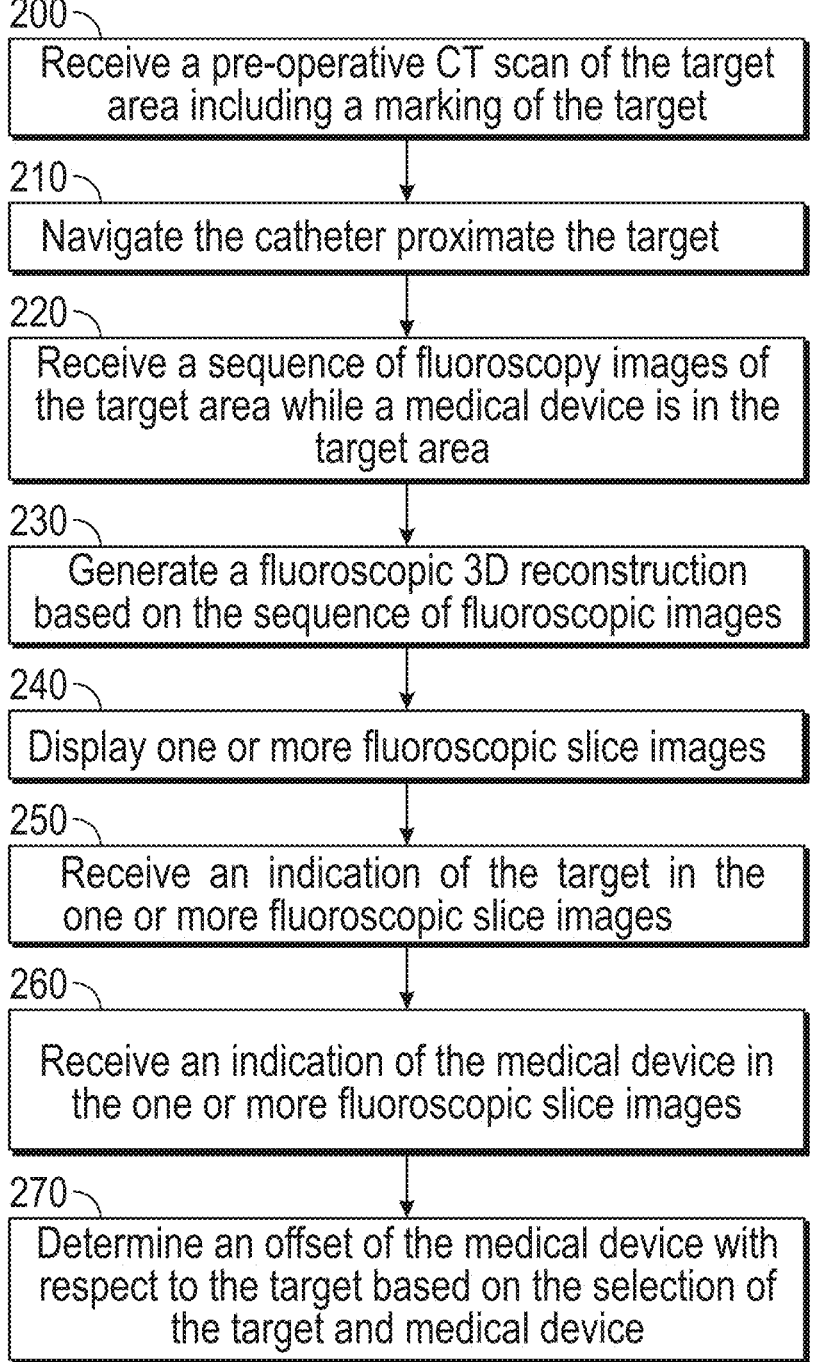

200
Receive a pre-operative CT scan of the target
area including a marking of the target 210
Navigate the catheter proximate the target 220
Receive a sequence of fluoroscopy images of
the target area while a medical device is in the
target area 230
Generate a fluoroscopic 3D reconstruction
based on the sequence of fluoroscopic images 240
Display one or more fluoroscopic slice images 250
Receive an indication of the target in the
one or more fluoroscopic slice images 260
Receive an indication of the medical device in
the one or more fluoroscopic slice images 270
Determine an offset of the medical device with
respect to the target based on the selection of
the target and medical device

FIG. 2

SYSTEM FOR FLUOROSCOPIC TRACKING OF A CATHETER TO UPDATE THE RELATIVE POSITION OF A TARGET AND THE CATHETER IN A 3D MODEL OF A LUMINAL NETWORK

CROSS-REFERENCE TO RELATED APPLICATION

This application is a divisional of U.S. patent application Ser. No. 16/742,141, filed on Jan. 14, 2020, which claims the benefit of, and priority to, U.S. Provisional Patent Application Ser. No. 62/799,822, filed on Feb. 1, 2019, the entire content of each of which is incorporated by reference herein.

BACKGROUND

Technical Field

This disclosure relates to the field of identifying and marking a target in fluoroscopic images and confirming the placement of tools such as biopsy or ablation tools in the target.

Description of Related Art

There are several commonly applied medical methods, such as endoscopic procedures or minimally invasive procedures, for treating various maladies affecting organs including the liver, brain, heart, lung, gall bladder, kidney and bones. Often, one or more imaging modalities, such as magnetic resonance imaging (MRI), ultrasound imaging, computed tomography (CT), fluoroscopy as well as others are employed by clinicians to identify and navigate to areas of interest within a patient and ultimately a target for treatment. In some procedures, pre-operative scans may be utilized for target identification and intraoperative guidance. However, real-time imaging may be often required to obtain a more accurate and current image of the target area. Furthermore, real-time image data displaying the current location of a medical device with respect to the target and its surrounding may be required to navigate the medical device to the target in a more safe and accurate manner (e.g., with unnecessary or no damage caused to other organs or tissue).

To enable an endoscopic, and more particularly the bronchoscopic approach in the lungs, endobronchial navigation systems have been developed that use previously acquired MRI data or CT image data to generate a three-dimensional (3D) rendering, model or volume of the particular body part such as the lungs. The resulting volume generated from the MRI scan or CT scan is then utilized to create a navigation plan to facilitate the advancement of a navigation catheter (or other suitable medical device) through a bronchoscope and a branch of the bronchus of a patient to an area of interest.

However, a three-dimensional volume of a patient's lungs, generated from previously acquired scans, such as CT scans, may not provide a basis sufficient for accurate guiding of medical instruments to a target during a navigation procedure. Accordingly, improvements are desired.

SUMMARY

One aspect of the disclosure is directed to a system for confirming placement of a biopsy tool in a target including: a navigation component configured to track a position of a catheter navigated into a luminal network. The system also includes a catheter configured to receive a biopsy tool; and a processor and one or more storage devices having stored thereon instructions. The instruction when executed by the processor, cause the processor to receive a first plurality of fluoroscopic images, generate a first fluoroscopic three-dimensional (3D) reconstruction from the plurality of fluoroscopic images. The system also includes present a first slice of the 3D reconstruction depicting the catheter in relation to a target visible in the slice of the 3D reconstruction. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The system where the navigation component is configured to correspond the position of the catheter to a three-dimensional (3D) model of the luminal network and the 3D model of the luminal network is generated from a pre-procedure computed tomography image data set. The system where a target can be identified in the 3D model of the luminal network. The system where the navigation component is an electro-magnetic navigation system. The system where the catheter is navigable to a position proximate the target. The system where the one or more storage devices have stored thereon further instructions, which when executed by the processor, cause the processor to: receive a second plurality of fluoroscopic images. The system may also include generate a second fluoroscopic three-dimensional reconstruction from the plurality of fluoroscopic images. The system may also include present a second slice of the 3D reconstruction depicting the catheter. The system may also include receive an indication of the location of the tip of the catheter in the slice of the 3D reconstruction. The system may also include present a third slice of the 3D reconstruction depicting a target location. The system may also include receive an indication of the location of the target in the third slice of the 3D reconstruction. The system may also include update a relative position of the target and the catheter in a 3D model of the luminal network. The system where, after updating the relative position, the catheter is navigated to the target and a biopsy tool is inserted into the target. The system where the second and third slices of the 3D reconstruction are generated from the second fluoroscopic three-dimensional reconstruction. The system where the one or more storage devices have stored thereon further instructions, which when executed by the processor, cause the processor to receive an indication of the location of the target in a fourth slice of the 3D reconstruction, the fourth slice of the 3D reconstruction being generated from the second fluoroscopic three-dimensional reconstruction. The system where the first, second, third, and fourth slices of the 3D reconstruction are presented on a user interface. The system where the third and fourth slices of the 3D reconstruction depict images of the target at different relative angles. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a method for confirming placement of a biopsy tool in a target. The method includes receiving a first plurality of fluoroscopic images and generating a first fluoroscopic three-dimensional (3D) reconstruction from the plurality of fluoroscopic images. The method also includes presenting a first slice of the 3D reconstruction depicting a catheter in relation to a target visible in the slice of the 3D reconstruction. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including receiving an indication of a position of the target. The method further including receiving a second plurality of fluoroscopic images, generating a second fluoroscopic three-dimensional (3D) reconstruction from the plurality of fluoroscopic images, presenting a second slice of the 3D reconstruction depicting a catheter, receiving an indication of the location of a tip of the catheter in the second slice of the 3D reconstruction, presenting a third slice of the 3D reconstruction depicting the target, receiving an indication of the location of the target in the third slice of the 3D reconstruction, and updating the relative position of the target and the catheter in a 3D model of a luminal network. The method where, after updating of the relative position, the catheter is navigated to the target and a biopsy tool is inserted into the target. The method where the second and third slices of the 3D reconstruction are generated from the second fluoroscopic three-dimensional reconstruction. The method further including receiving an indication of the location of the target in a fourth slice of the 3D reconstruction, the fourth slice of the 3D reconstruction being generated from the second fluoroscopic three-dimensional reconstruction. The method where the first, second, third, and fourth slices of the 3D reconstruction are presented on a user interface. The method where the third and fourth slices of the 3D reconstruction depict images of the target at different relative angles. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

Yet another aspect of the disclosure is directed to a system including: a computer readable recording medium storing thereon instructions, and a processor configured to access the instructions and when the instructions are executed by the processor cause the processor to receive a first plurality of fluoroscopic images and generate a first fluoroscopic three-dimensional (3D) reconstruction from the plurality of fluoroscopic images. The system also presents a first slice of the 3D reconstruction depicting a catheter in relation to a target to which the catheter had been navigated visible in the slice of the 3D reconstruction. Other embodiments of this aspect include corresponding computer systems, apparatus, and computer programs recorded on one or more computer storage devices, each configured to perform the actions of the methods and systems described herein.

Any of the above aspects and embodiments of the disclosure may be combined without departing from the scope of the disclosure.

BRIEF DESCRIPTION OF THE DRAWINGS

Various aspects and embodiments of the disclosure are described hereinbelow with references to the drawings, wherein:

FIG. 2 is a flow chart of a method for identifying and marking a target in fluoroscopic 3D reconstruction in accordance with the disclosure;

DETAILED DESCRIPTION

This disclosure is directed to identifying and marking a target in fluoroscopic images and confirming the placement of tools such as biopsy or ablation tools in the target. In accordance with confirming the placement of tools in a target, the disclosure describes systems, methods and computer program products for facilitating the identification and marking of a target in real-time fluoroscopic images using a standard fluoroscope.

Figure 1:
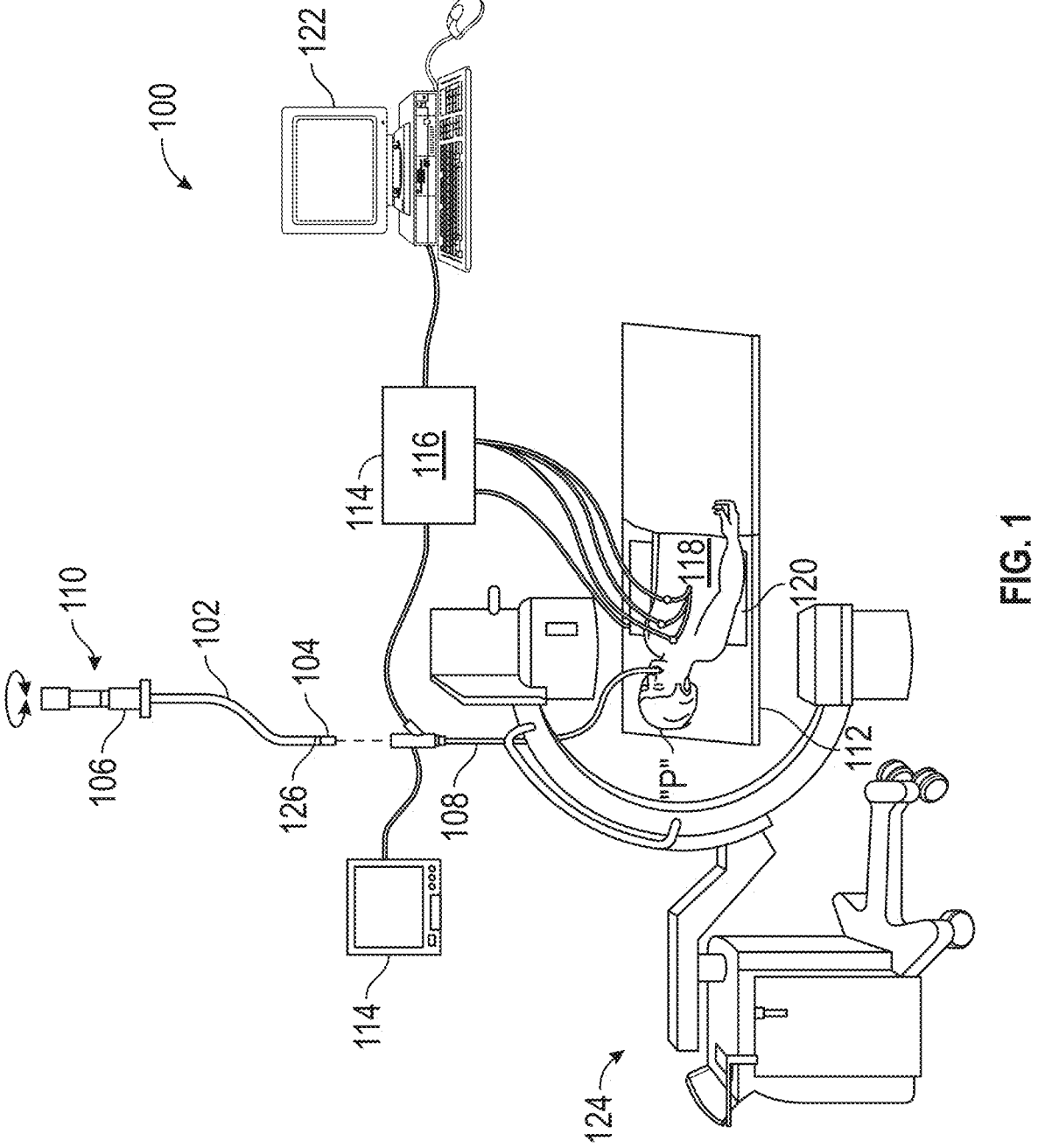
FIG. 1 is a perspective view of a system for navigating to a soft-tissue target via the airways network in accordance with the disclosure.

In accordance with aspects of the disclosure, the confirmation of the "tool-in-target" is a portion of a larger workflow of an electromagnetic navigation system. FIG. 1 is a perspective view of an exemplary system for facilitating navigation to a soft-tissue target via the airways network. System 100 may be further configured to construct fluoroscopic based three-dimensional (3D) volumetric data of the target area from two-dimensional (2D) fluoroscopic images. System 100 may be further configured to facilitate approach of a medical device to the target area by using Electromagnetic Navigation Bronchoscopy (ENB) and for determining the location of a medical device with respect to the target.

One aspect of the system 100 is a software component for reviewing computed tomography (CT) image data that has been acquired separately from system 100. The review of the CT image data allows a user to identify one or more targets, plan a pathway to an identified target (planning phase), navigate an catheter 102 which may act in some embodiments as an extended working channel (EWC) of an endoscope to the target (navigation phase) using a user interface, and confirming placement of a sensor 104 relative to the target. One such EMN system is the ELECTROMAGNETIC NAVIGATION BRONCHOSCOPY® system currently sold by Medtronic PLC. The target may be tissue of interest identified by review of the CT image data during the planning phase. Following navigation, a medical device, such as a biopsy tool or other tool, may be inserted into catheter 102 to obtain a tissue sample from the tissue located at, or proximate to, a target.

As shown in FIG. 1, catheter 102 is part of a catheter guide assembly 106. In practice, catheter 102 is inserted into a bronchoscope 108 for access to a luminal network of the patient "P." Specifically, catheter 102 of catheter guide assembly 106 may be inserted into a working channel of a bronchoscope 108 for navigation through a patient's luminal network. A locatable guide (LG) 110, including a sensor 104 is inserted into catheter 102 and locked into position such that sensor 104 extends a desired distance beyond the distal tip of catheter 102. The position and orientation of sensor 104 relative to the reference coordinate system, and thus the distal portion of catheter 102, within an electromagnetic field can be derived. Catheter guide assemblies 106 are currently marketed and sold by Medtronic PLC under the brand names SUPERDIMENSION® Procedure Kits, or EDGE™ Procedure Kits, and are contemplated as useable with the disclosure.

System 100 generally includes an operating table 112 configured to support a patient "P," a bronchoscope 108 configured for insertion through the patient "P" 's mouth into the patient "P" 's airways; monitoring equipment 114 coupled to bronchoscope 108 (e.g., a video display, for displaying the video images received from the video imaging system of bronchoscope 108); a locating or tracking system 114 including a locating or tracking module 116; a plurality of reference sensors 118; a transmitter mat 120 including a plurality of incorporated markers (not shown); and a computing device 122 including software and/or hardware used to facilitate identification of a target, pathway planning to the target, navigation of a medical device to the target, and/or confirmation and/or determination of placement of catheter 102, or a suitable device therethrough, relative to the target. Computing device 122 may be similar to workstation 80 of FIG. 6 and may be configured to execute the methods of FIG. 2 and FIG. 4.

A fluoroscopic imaging device 124 capable of acquiring fluoroscopic or x-ray images or video of the patient "P" is also included in this particular aspect of system 100. The images, sequence of images, or video captured by fluoroscopic imaging device 124 may be stored within fluoroscopic imaging device 124 or transmitted to computing device 122 for storage, processing, and display. Additionally, fluoroscopic imaging device 124 may move relative to the patient "P" so that images may be acquired from different angles or perspectives relative to patient "P" to create a sequence of fluoroscopic images, such as a fluoroscopic video. The pose of fluoroscopic imaging device 124 relative to patient "P" while capturing the images may be estimated via markers incorporated with the transmitter mat 120. The markers are positioned under patient "P", between patient "P" and operating table 112, and between patient "P" and a radiation source or a sensing unit of fluoroscopic imaging device 124. The markers incorporated with the transmitter mat 120 may be two separate elements which may be coupled in a fixed manner or alternatively may be manufactured as a single unit. Fluoroscopic imaging device 124 may include a single imaging device or more than one imaging device.

Computing device 122 may be any suitable computing device including a processor and storage medium, wherein the processor is capable of executing instructions stored on the storage medium. Computing device 122 may further include a database configured to store patient data, CT data sets including CT images, fluoroscopic data sets including fluoroscopic images and video, fluoroscopic 3D reconstruction, navigation plans, and any other such data. Although not explicitly illustrated, computing device 122 may include inputs, or may otherwise be configured to receive CT data sets, fluoroscopic images/video, and other data described herein. Additionally, computing device 122 includes a display configured to display graphical user interfaces. Computing device 122 may be connected to one or more networks through which one or more databases may be accessed.

With respect to the planning phase, computing device 122 utilizes previously acquired CT image data for generating and viewing a three-dimensional model or rendering of the patient "P" 's airways, enables the identification of a target on the three-dimensional model (automatically, semi-automatically, or manually), and allows for determining a pathway through the patient "P" 's airways to tissue located at and around the target. More specifically, CT images acquired from previous CT scans are processed and assembled into a three-dimensional CT volume, which is then utilized to generate a three-dimensional model of the patient "P" 's airways. The three-dimensional model may be displayed on a display associated with computing device 122, or in any other suitable fashion. Using computing device 122, various views of the three-dimensional model or enhanced two-dimensional images generated from the three-dimensional model are presented. The enhanced two-dimensional images may possess some three-dimensional capabilities because they are generated from three-dimensional data. The three-dimensional model may be manipulated to facilitate identification of target on the three-dimensional model or two-dimensional images, and selection of a suitable pathway through the patient "P" 's airways to access tissue located at the target can be made. Once selected, the pathway plan, three-dimensional model, and images derived therefrom, can be saved and exported to a navigation system for use during the navigation phase or phases. One such planning software is the ILLUMISITE planning suite currently sold by Medtronic PLC.

With respect to the navigation phase, a six degrees-of-freedom electromagnetic locating or tracking system 114, or other suitable system for determining location or position, is utilized for performing registration of the images and the pathway for navigation, although other configurations are also contemplated. Tracking system 114 includes the tracking module 116, a plurality of reference sensors 118, and the transmitter mat 120 (including the markers). Tracking system 114 is configured for use with a locatable guide 110 and sensor 104. As described above, locatable guide 110 and sensor 104 are configured for insertion through catheter 102 into a patient "P" 's airways (either with or without bronchoscope 108) and are selectively lockable relative to one another via a locking mechanism.

Transmitter mat 120 is positioned beneath patient "P." Transmitter mat 120 generates an electromagnetic field around at least a portion of the patient "P" within which the position of a plurality of reference sensors 118 and the sensor 104 can be determined with use of a tracking module 116. A second electromagnetic sensor 126 may also be incorporated into the end of the catheter 102. Sensor 126 may be a five degree of freedom (5 DOF) sensor or a six degree of freedom (6 DOF) sensor. One or more of reference sensors 118 are attached to the chest of the patient "P." The six degrees of freedom coordinates of reference sensors 118 are sent to computing device 122 (which includes the appropriate software) where they are used to calculate a patient coordinate frame of reference. Registration is generally performed to coordinate locations of the three-dimensional model and two-dimensional images from the planning phase, with the patient "P" 's airways as observed through the bronchoscope 108, and allow for the navigation phase to be undertaken with precise knowledge of the location of the sensor 104, even in portions of the airway where the bronchoscope 108 cannot reach.

Registration of the patient "P" 's location on the transmitter mat 120 is performed by moving sensor 104 through the airways of the patient "P." More specifically, data pertaining to locations of sensor 104, while locatable guide 110 is moving through the airways, is recorded using transmitter mat 120, reference sensors 118, and tracking system 114. A shape resulting from this location data is compared to an interior geometry of passages of the three-dimensional model generated in the planning phase, and a location correlation between the shape and the three-dimensional model based on the comparison is determined, e.g., utilizing the software on computing device 122. In addition, the software identifies non-tissue space (e.g., air filled cavities) in the three-dimensional model. The software aligns, or registers, an image representing a location of sensor 104 with the three-dimensional model and/or two-dimensional images generated from the three-dimension model, which are based on the recorded location data and an assumption that locatable guide 110 remains located in non-tissue space in the patient "P" 's airways. Alternatively, a manual registration technique may be employed by navigating the bronchoscope 108 with the sensor 104 to pre-specified locations in the lungs of the patient "P", and manually correlating the images from the bronchoscope to the model data of the three-dimensional model.

Though described herein with respect to EMN systems using EM sensors, the instant disclosure is not so limited and may be used in conjunction with flexible sensor, ultrasonic sensors, or without sensors. Additionally, the methods described herein may be used in conjunction with robotic systems such that robotic actuators drive the catheter 102 or bronchoscope 108 proximate the target.

Following registration of the patient "P" to the image data and pathway plan, a user interface is displayed in the navigation software which sets for the pathway that the clinician is to follow to reach the target. Once catheter 102 has been successfully navigated proximate the target as depicted on the user interface, the locatable guide 110 may be unlocked from catheter 102 and removed, leaving catheter 102 in place as a guide channel for guiding medical devices including without limitation, optical systems, ultrasound probes, marker placement tools, biopsy tools, ablation tools (i.e., microwave ablation devices), laser probes, cryogenic probes, sensor probes, and aspirating needles to the target.

A medical device may be then inserted through catheter 102 and navigated to the target or to a specific area adjacent to the target. A sequence of fluoroscopic images may be then acquired via fluoroscopic imaging device 124, optionally by a user and according to directions displayed via computing device 122. A fluoroscopic 3D reconstruction may be then generated via computing device 122. The generation of the fluoroscopic 3D reconstruction is based on the sequence of fluoroscopic images and the projections of structure of markers incorporated with transmitter mat 120 on the sequence of images. One or more slices of the 3D reconstruction may be then generated based on the pre-operative CT scan and via computing device 122. The one or more slices of the 3D reconstruction and the fluoroscopic 3D reconstruction may be then displayed to the user on a display via computing device 122, optionally simultaneously. The slices of 3D reconstruction may be presented on the user interface in a scrollable format where the user is able to scroll through the slices in series. The user may be then directed to identify and mark the target while using the slice of the 3D reconstruction as a reference. The user may be also directed to identify and mark the medical device in the sequence of fluoroscopic 2D-dimensional images. An offset between the location of the target and the medical device may be then determined or calculated via computing device 122. The offset may be then utilized, via computing device 122, to correct the location of the medical device on the display with respect to the target and/or correct the registration between the three-dimensional model and tracking system 114 in the area of the target and/or generate a local registration between the three-dimensional model and the fluoroscopic 3D reconstruction in the target area.

FIG. 2 depicts the process of performing a local registration using system 100. In step 200, a pre-operative CT scan of the target area may be received by the computing device 122. The pre-operative CT scan that is received may include a pathway plan that has already been developed or the user may generate the pathway plan using computing device 122. At step 210 a user navigates the catheter 102 and sensor 104 proximate the target using the pathway plan which may be displayed on computing device 122 as part of the 3D model, described above.

Once proximate the target, the user may wish to confirm the exact relative positioning of the sensor 104 and the target. At step 220, a sequence of fluoroscopic images of the target area acquired in real time about a plurality of angles relative to the target area may be captured by fluoroscopic imaging device 124. The sequence of images may be captured while a medical device is positioned in the target area. In some embodiments, the method may include further steps for directing a user to acquire the sequence of fluoroscopic images. In some embodiments, the method may include one or more further steps for automatically acquiring the sequence of fluoroscopic images.

The real-time fluoroscopic images may be two-dimensional (2D) images, a three-dimensional (3D) reconstruction generated from a plurality of 2D images, or slice-images of a 3D reconstruction. The identification and marking of the target in the real-time fluoroscopic data may be facilitated by using synthetic or virtual fluoroscopic data, which includes a marking or an indication of the target, as a reference. The virtual fluoroscopic data may be generated from previously acquired volumetric data and preferably such that it would imitate, as much as possible, fluoroscopic-type data. Typically, the target is better shown in the imaging modality of the previously acquired volumetric data than in the real-time fluoroscopic data.

The disclosure refers to systems and methods for facilitating the navigation of a medical device to a target and/or a target area using real-time two-dimensional fluoroscopic images of the target area. The navigation is facilitated by using local three-dimensional volumetric data, in which small soft-tissue objects are visible, constructed from a sequence of fluoroscopic images captured by a standard fluoroscopic imaging device. The fluoroscopic-based constructed local three-dimensional volumetric data may be used to correct a location of a medical device with respect to a target or may be locally registered with previously acquired volumetric data. In general, the location of the medical device may be determined by a tracking system. The tracking system may be registered with the previously acquired volumetric data. A local registration of the real-time three-dimensional fluoroscopic data to the previously acquired volumetric data may be then performed via the tracking system. Such real-time data may be used, for example, for guidance, navigation planning, improved navigation accuracy, navigation confirmation, and treatment confirmation.

In some embodiments, receiving a fluoroscopic 3D reconstruction of a body region may include receiving a sequence of fluoroscopic images of the body region and generating the fluoroscopic 3D reconstruction of the body region based on at least a portion of the fluoroscopic images. In some embodiments, the method may further include directing a user to acquire the sequence of fluoroscopic images by manually sweeping the fluoroscope. In some embodiments, the method may further include automatically acquiring the sequence of fluoroscopic images. The fluoroscopic images may be acquired by a standard fluoroscope, in a continuous manner and about a plurality of angles relative to the body region. The fluoroscope may be swept manually, i.e., by a user, or automatically. For example, the fluoroscope may be swept along an angle of 20 to 45 degrees. In some embodiments, the fluoroscope may be swept along an angle of 30±5 degrees. Typically, these images are gathered in a fluoroscopic sweep of the fluoroscopic imaging device 124 of about 30 degrees (i.e., 15 degrees on both sides of the AP position). As is readily understood, larger sweeps of 45, 60, 90 or even greater angles may alternatively be performed to acquire the fluoroscopic images.

At step 230, a three-dimensional reconstruction of the target area may be generated based on the sequence of fluoroscopic images. In some embodiments, the method further comprises one or more steps for estimating the pose of the fluoroscopic imaging device while acquiring each of the fluoroscopic images, or at least a plurality of them. The three-dimensional reconstruction of the target area may be then generated based on the pose estimation of the fluoroscopic imaging device.

In some embodiments, the markers incorporated with the transmitter mat 120 may be placed with respect to the patient "P" and the fluoroscopic imaging device 124, such that each fluoroscopic image includes a projection of at least a portion of the structure of markers. The estimation of the pose of the fluoroscopic imaging device while acquiring each image may be then facilitated by the projections of the structure of markers on the fluoroscopic images. In some embodiments, the estimation may be based on detection of a possible and most probable projection of the structure of markers as a whole on each image.

Figure 3A:
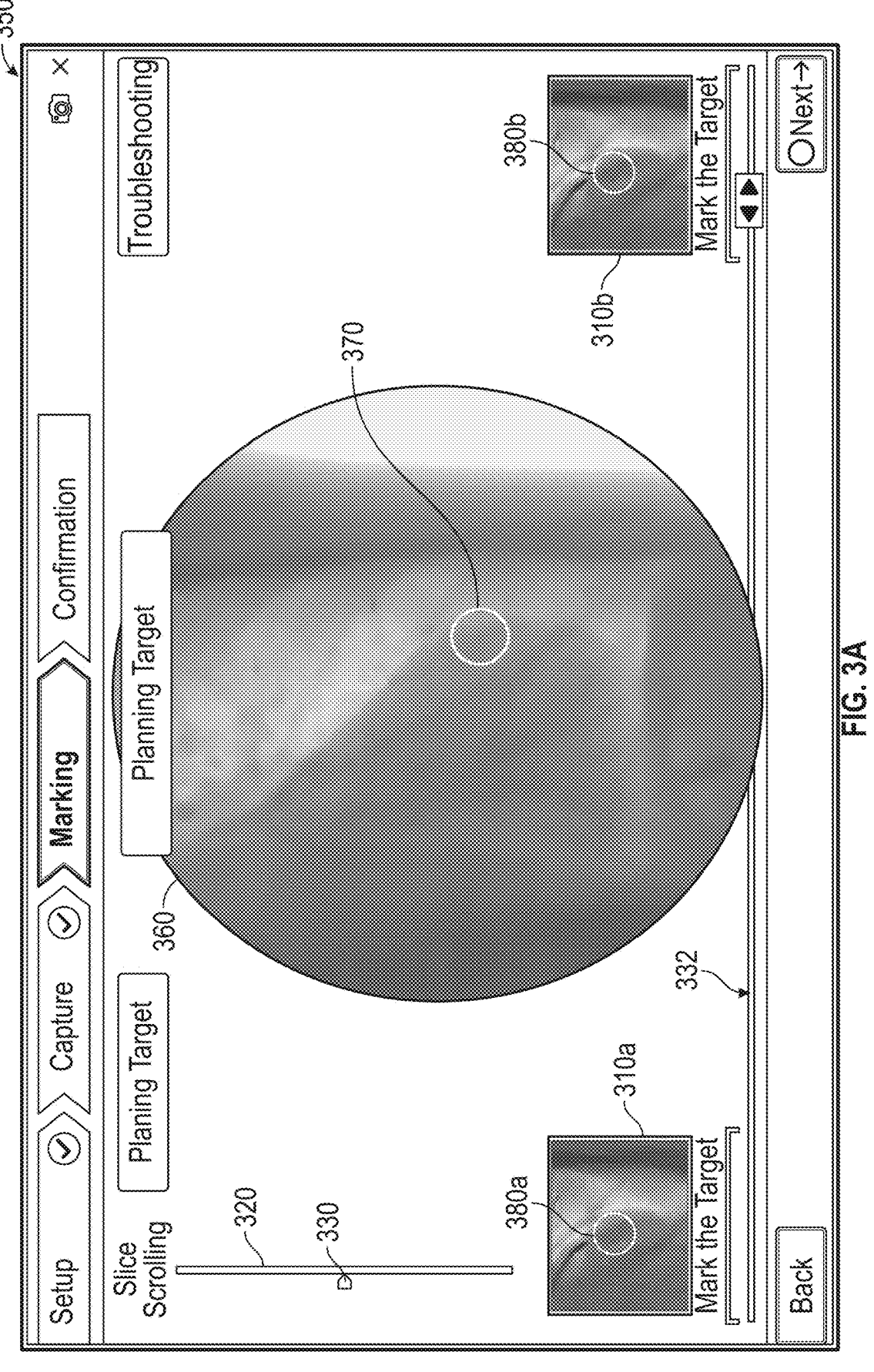
FIG. 3A is a screen shot of a user interface for marking a target in a fluoroscopic image in accordance with the disclosure.
Figure 3B:
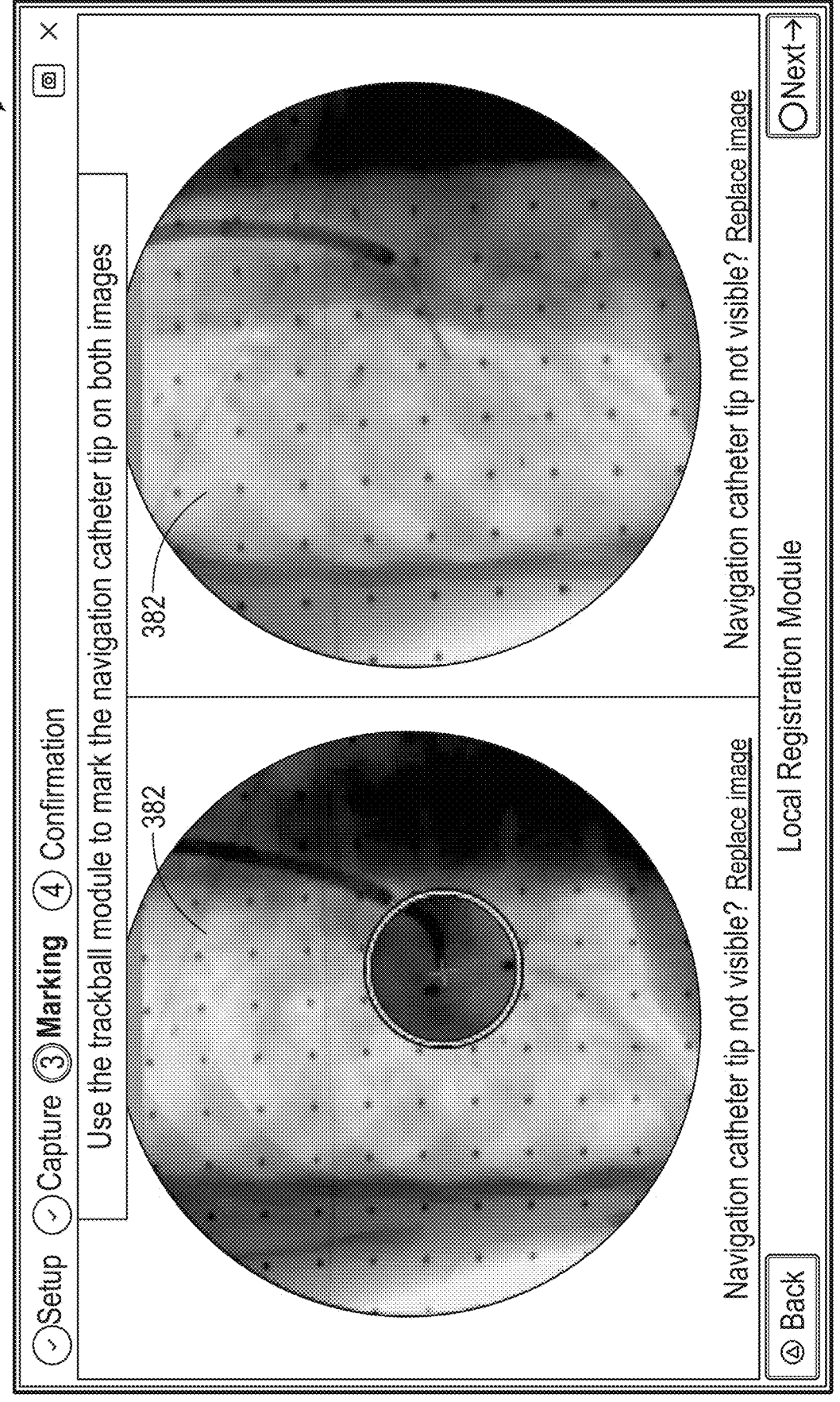
FIG. 3B is a screen shot of a user interface for marking a medical device target in a fluoroscopic image in accordance with the disclosure.

In step 240, one or more fluoroscopy images are displayed to a user as illustrated in FIGS. 3A and 3B. As depicted in FIG. 3A, which is an exemplary screen shot 350 of a software program running on computing device 122, a slice of the 3D reconstruction 360 is displayed simultaneously with two thumbnail images 310a and 310b of a fluoroscopic 3D reconstruction in accordance with the disclosure. As noted above, the 3D reconstruction is created for a fluoroscopic sweep of images between 30 and 90 degrees. By using the scroll bar 320 and indicator 330, the slice of the 3D reconstruction 360 depicted on screen shot 350 changes in accordance with the movement.

In some embodiments, the generation of the virtual fluoroscopy slice image may be generated according to the following steps. In a first step, the received CT volume is aligned with the fluoroscopic 3D reconstruction. In a second step, an estimation of a pose of the fluoroscopic device while capturing the set of fluoroscopic images used to generate the fluoroscopic 3D reconstruction in a selected position, e.g., in AP (anteroposterior) position, with respect to the target or patient is received or calculated. In a third step, a slice or slices of the CT scan volume perpendicular to the selected position and which include the target are generated. In a fourth step, the CT slice or slices are projected according to the estimated fluoroscope pose to receive a virtual fluoroscopy slice image.

In some embodiments, generation of a virtual fluoroscopy slice image of the target area may include the following steps. In a first step, virtual fluoroscope poses around the target may be obtained. In some embodiments, the virtual fluoroscope poses may be generated by simulating a fluoroscope trajectory while the fluoroscope scans the target. In some embodiments, the method may further include the generation of the 3D fluoroscopic reconstruction, as described with respect to step 430 of FIG. 4. The estimated poses of the fluoroscopic device while capturing the sequence of fluoroscopic images used to generate the fluoroscopic 3D reconstruction may then be utilized. In a second step, slices of the 3D reconstruction may be generated by projecting the CT scan volume according to the virtual fluoroscope poses. In a third step, a virtual fluoroscopic 3D reconstruction may be generated based on the slices of the 3D reconstruction. In some embodiments, the virtual fluoroscopic 3D reconstruction may be generated while using the method of reconstruction of the 3D fluoroscopic volume with adaptations. The resulting virtual fluoroscopic volume may then look more like the fluoroscopic volume.

In some embodiments, when marking of the target in a slice image of a fluoroscopic 3D reconstruction is desired, generating and using a virtual slice image as a reference may be more advantageous. In some embodiments, when marking of the target in a fluoroscopic 2D image is desired, generating and using a virtual fluoroscopic 2D image may be more advantageous.

In accordance with step 250, a selection of the target from the fluoroscopic 3D reconstruction is made by the user. As shown in FIG. 3A, at two end portions of the fluoroscopic 3D reconstruction displayable on screen shot 350, the user is asked to "mark the target" in the slice of the 3D reconstruction 360. These two ends could be any two positions of the fluoroscopic sweep, so long as they are sufficiently angularly separated such that efficient triangulation of the location of the target and the catheter (FIG. 3B) can be performed.

As shown in FIG. 3A, the user had previously marked the target at one end of the sweep, depicted in thumbnail image 310a, and is in the process of marking the target in a second end of the sweep, with the current slice of the 3D reconstruction 360 which is depicted in thumbnail image 310b. At the bottom of the screen shot 350, two ranges are defined within which the user is to "mark the target" in an image that appears within a range. A second scroll bar 332 on the bottom of the screen shot 350 allows the user to view the virtual fluoroscopy images 360 as a video rather than to scroll through the slices individually using scroll bar 320. In addition, the software may be configured to automatically jump the user from one "mark the target" range to the other following successful marking in the first "mark the target" range.

As depicted in FIG. 3A, the user has placed a marker 370 on the slice of the 3D reconstruction 360. This marker also appears in thumbnail image 310b as marker 380b. In this manner, at step 240 the user has marked the location of the target in the fluoroscopic image data collected by the fluoroscopic imaging device 124.

In step 260, a selection of the medical device from the three-dimensional reconstruction or the sequence of fluoroscopic images is made. In some embodiments, this may be automatically made, and a user either accepts or rejects the selection. In some embodiments, the selection is made directly by the user. As depicted in FIG. 3B, the user may be asked to mark the location of the catheter 102. FIG. 3B depicts a screen shot 380 including two actual fluoroscopic images 382. The user is asked to mark the end of the catheter 102 in each of the actual fluoroscopic images 382. Each of these images comes from portions of the sweep that correspond to the "mark the target" portions depicted in FIG. 3A.

Once both the catheter 102 and the target are marked at both ends of the sweep, at step 270, an offset of the catheter 102 with respect to the target may be calculated. The determination of the offset is based on the received selections of the target and the medical device. This offset is used to update the detected position of the catheter 102, and specifically the sensor 104 in the 3D model and the pathway plan that was created to navigate to the target.

Typically, at this point in the procedure, the user has managed to navigate the catheter 102 to within 2-3 cm of the target, for example. With the updated position provided by the fluoroscopic data collection and position determination, the user can have confidence of reaching the target while traversing this last distance.

In heretofore known systems, the sensor 104 would now be removed from the catheter 102 and the final approaches to the target in navigation would proceed completely blind. Recently, systems have been devised that allow for the incorporation of a sensor 126 that can provide 5 DOF location information of the catheter 102 after the sensor 104 is removed.

Following removal of the sensor 104, a tool, such as a needle or coring biopsy tool, brushes, ablation devices (e.g., RF, microwave, chemical, radiological, etc.), clamping devices, and others, may be advanced down the catheter 102. In one example, a biopsy tool (not shown) is advanced down the catheter 102 and, using the sensor 126, the user navigates the final 2-3 cm, for example, to the target and can advance to biopsy tool into the target as it appears in the 3D model. However, despite the confidence provided by updating relative locations of the target and the catheter 102, there are times where a user may wish to confirm that the biopsy tool is in fact placed within the target.

To undertake this tool-in-target confirmation, a second fluoroscopic imaging process can be undertaken. As part of this process, the user can select a "tool-in target" tab on the user interface at step 410 of the method 400 of FIG. 4. This selection can initiate the fluoroscopic imaging device 124. At step 410, the user may also be directed to perform a fluoroscopic sweep similar to that described previously. The images collected during the fluoroscopic sweep can be processed to form a fluoroscopic 3D reconstruction step 420.

Figure 5:
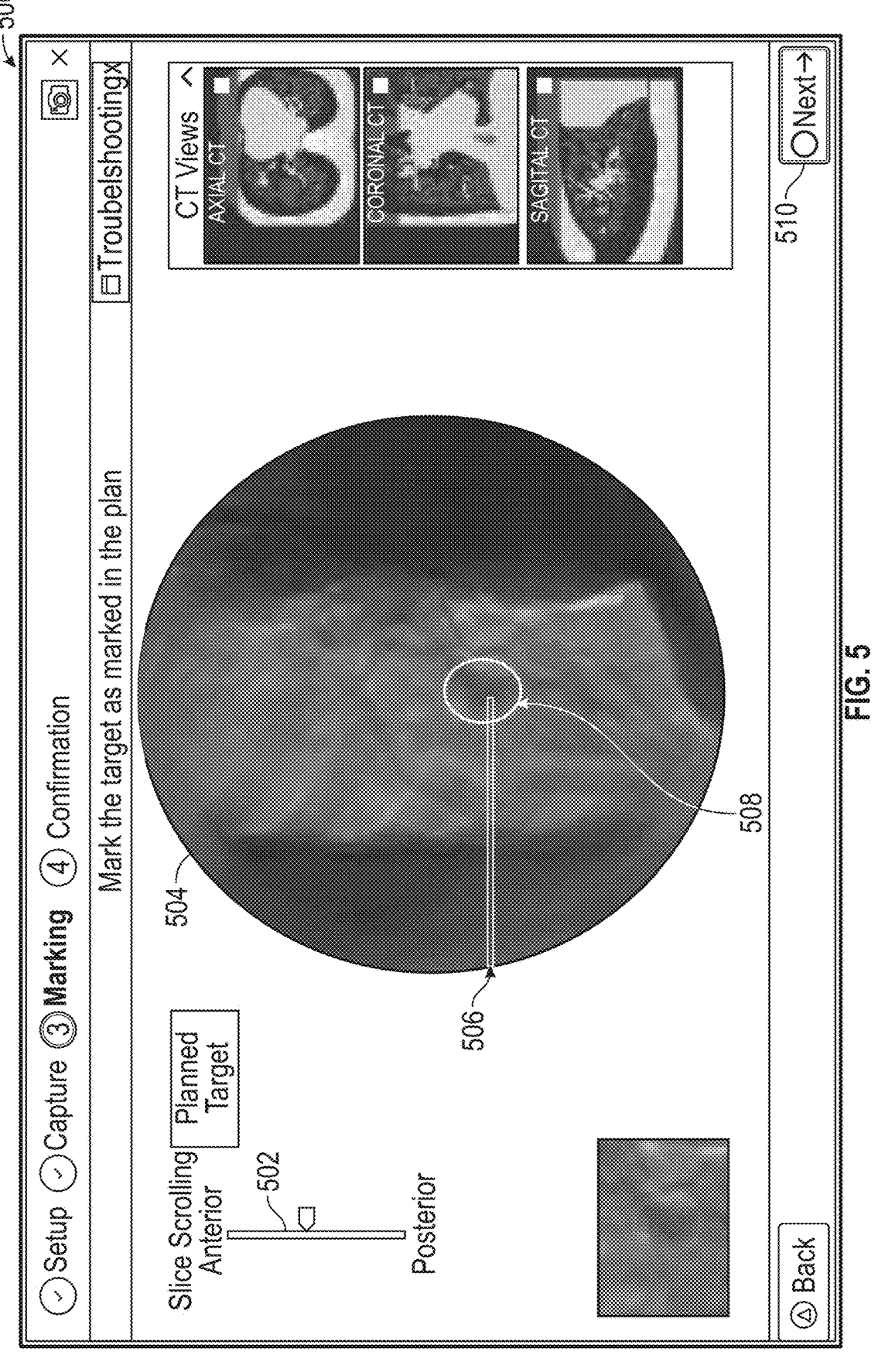
FIG. 5 is a screen shot of a user interface for confirming placement of a biopsy tool in a target in accordance with the disclosure.

A slice of the 3D reconstruction is generated from the fluoroscopic 3D reconstruction and output as screenshot 500 as depicted in FIG. 5 in step 430. The screen shot 500 is similar to that of FIG. 3A. The user is able to use the scroll bar 502 to scroll through the slices of the 3D reconstruction 504. The biopsy tools are typically made of metal and other materials which resolve quite well in fluoroscopic images. As a result, the user can scroll through the slices of the 3D reconstruction 504 all along the sweep to ensure that the biopsy tool is in the target indicated by marker 508 at step 440.

As an alternative to step 440 where the user scrolls through the slices of the 3D reconstruction 504, the user may be requested to mark the position of the catheter 102 similar to the step described in step 260 (FIG. 2) in a 2D fluoroscopic image acquired by the fluoroscopic imaging device 124 as part of its fluoroscopic sweep from step 410. This step may also be performed automatically via image processing techniques by computing device 122. After receiving the marked position of the catheter 102, the 3D coordinates of the marked position can be determined by the computing device 122. Accordingly, the computing device 122 can identify a slice of the 3D reconstruction 504 that best displays the catheter 102. Additionally, or alternatively, this marking of the position of the catheter 102 in the 2D fluoroscopic image provides an indication of the position of the catheter 102 in the 3D reconstruction 504, which can then be presented to the user for review. Still further, the user may be asked to mark the target in the 2D fluoroscopic image and a 3D relative position of the target and the catheter 102 or biopsy tool 506 can be calculated and displayed in the 3D reconstruction 504, similar that that described above with reference to FIG. 2.

In addition to the above, with respect to depiction of the catheter 102 in the slice images of the 3D reconstruction 504, image processing techniques can be employed to enhance the display of the catheter 102 or biopsy tool 506 extending therethrough. These techniques may further be employed to remove artifacts that might be the result of the reconstruction process.

Figure 4:
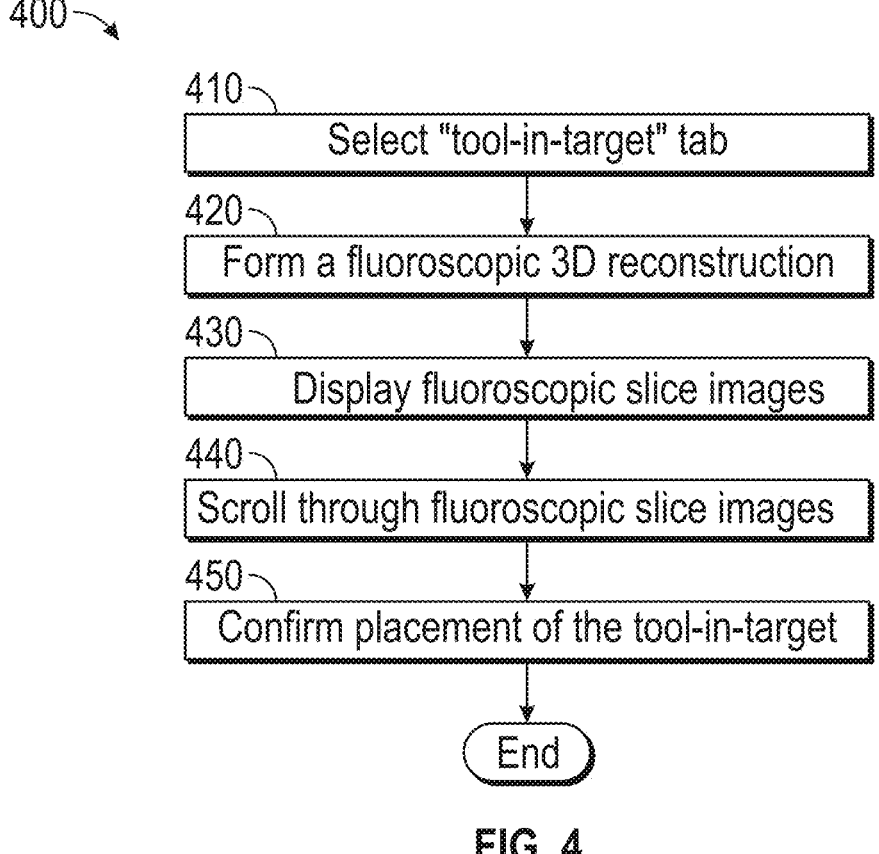
FIG. 4 is a flow chart of a method for confirming placement of a biopsy tool in a target in accordance with the disclosure.

If the user is satisfied with the position of the biopsy tool 506, the user can click the next button 510 to confirm placement of the tool-in-target at step 450, thereby ending the tool-in-target confirmation method 400 of FIG. 4. Then, the user can proceed back to the 3D model and perform navigation to other targets. Additionally, if more biopsies are desired, following each movement of the catheter 102 and biopsy tool 506, one could perform another tool-in-lesion confirmation starting again at step 410. Though not necessarily required, the system may prompt the user to identify the location of the target in the images, though most users can perform their confirmation of the tool-in-lesion without requiring a separate indication of the target.

Figure 6:
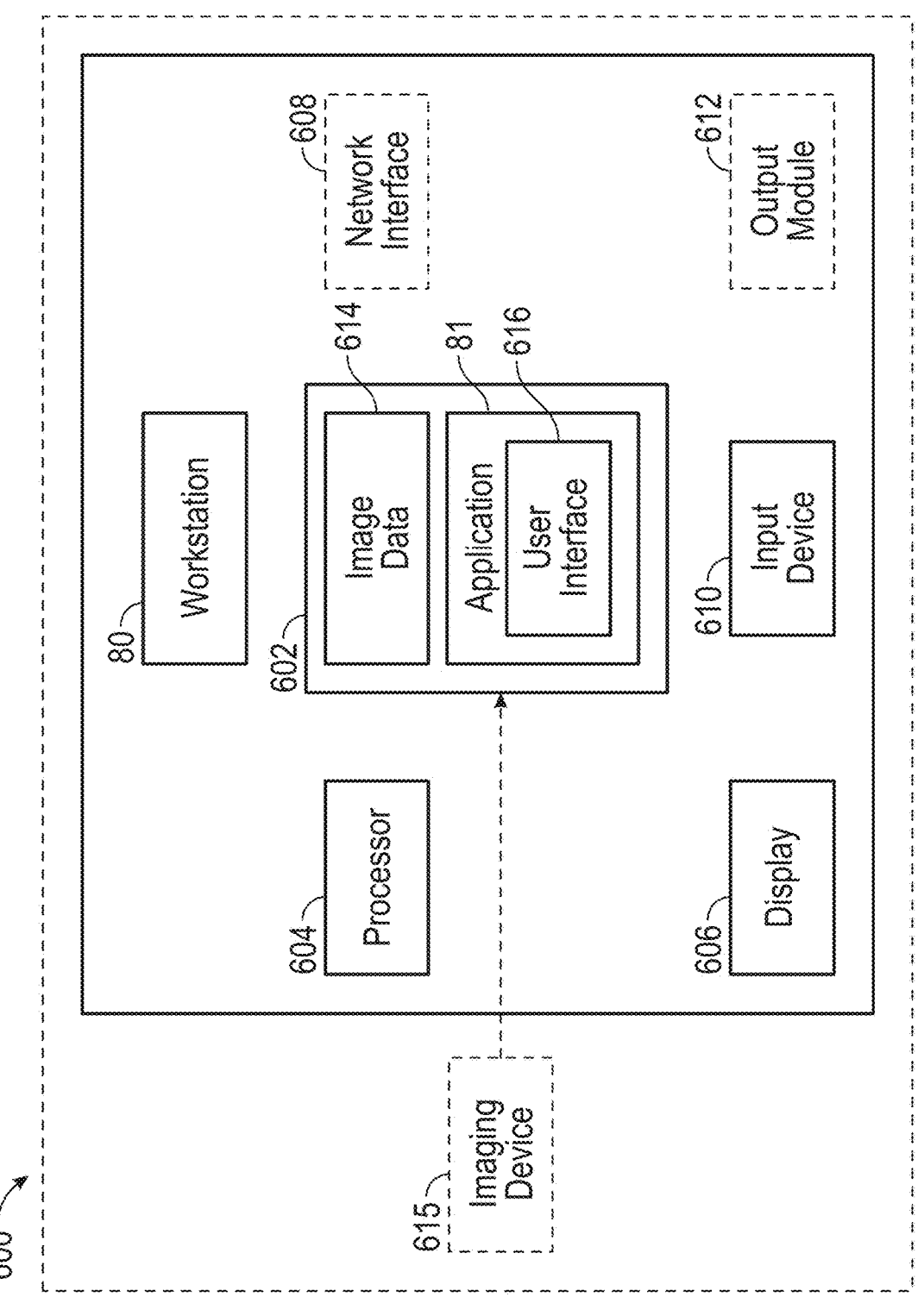
FIG. 6 is a schematic view of a system in accordance with the disclosure for navigating to a target and displaying the user interfaces in accordance with the disclosure.

Reference is now made to FIG. 6, which is a schematic diagram of a system 600 configured for use with the methods of FIGS. 2 and 4. System 600 may include a workstation 80, and optionally a fluoroscopic imaging device or fluoroscope 615. In some embodiments, workstation 80 may be coupled with fluoroscope 615, directly or indirectly, e.g., by wireless communication. Workstation 80 may include a memory or storage device 602, a processor 604, a display 606 and an input device 610. Processor or hardware processor 604 may include one or more hardware processors. Workstation 80 may optionally include an output module 612 and a network interface 608. Memory 602 may store an application 81 and image data 614. Application 81 may include instructions executable by processor 604 for executing the method steps of FIGS. 2 and 4. Application 81 may further include a user interface 616. Image data 614 may include the CT scan, the fluoroscopic 3D reconstructions of the target area and/or any other fluoroscopic image data and/or the generated one or more virtual fluoroscopy images. Processor 604 may be coupled with memory 602, display 606, input device 610, output module 612, network interface 608 and fluoroscope 615. Workstation 80 may be a stationary computing device, such as a personal computer, or a portable computing device such as a tablet computer. Workstation 80 may embed a plurality of computer devices.

Memory 602 may include any non-transitory computer-readable storage media for storing data and/or software including instructions that are executable by processor 604 and which control the operation of workstation 80 and, in some embodiments, may also control the operation of fluoroscope 615. Fluoroscope 615 may be used to capture a sequence of fluoroscopic images based on which the fluoroscopic 3D reconstruction is generated. In an embodiment, memory or storage device 602 may include one or more storage devices such as solid-state storage devices, e.g., flash memory chips. Alternatively, or in addition to the one or more solid-state storage devices, memory 602 may include one or more mass storage devices connected to the processor 604 through a mass storage controller (not shown) and a communications bus (not shown).

Although the description of computer-readable media contained herein refers to solid-state storage, it should be appreciated by those skilled in the art that computer-readable storage media can be any available media that can be accessed by the processor 604. That is, computer readable storage media may include non-transitory, volatile and non-volatile, removable and non-removable media implemented in any method or technology for storage of information such as computer-readable instructions, data structures, program modules or other data. For example, computer-readable storage media may include RAM, ROM, EPROM, EEPROM, flash memory or other solid-state memory technology, CD-ROM, DVD, Blu-Ray or other optical storage, magnetic cassettes, magnetic tape, magnetic disk storage or other magnetic storage devices, or any other medium which may be used to store the desired information, and which may be accessed by workstation 80.

Application 81 may, when executed by processor 604, cause display 606 to present user interface 616. User interface 616 may be configured to present to the user the fluoroscopic 3D reconstruction and the generated virtual fluoroscopy image, as shown, for example, in FIG. 3A. User interface 616 may be further configured to direct the user to identify and mark the target in the displayed fluoroscopic 3D reconstruction or any other fluoroscopic image data in accordance with the disclosure.

Network interface 608 may be configured to connect to a network such as a local area network (LAN) consisting of a wired network and/or a wireless network, a wide area network (WAN), a wireless mobile network, a Bluetooth network, and/or the Internet. Network interface 608 may be used to connect between workstation 80 and fluoroscope 615. Network interface 608 may be also used to receive image data 614. Input device 610 may be any device by which a user may interact with workstation 80, such as, for example, a mouse, keyboard, foot pedal, touch screen, and/or voice interface. Output module 612 may include any connectivity port or bus, such as, for example, parallel ports, serial ports, universal serial busses (USB), or any other similar connectivity port known to those skilled in the art.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A method for confirming placement of a biopsy tool in a target, comprising:
   receiving a first plurality of fluoroscopic images;
   generating a first fluoroscopic three-dimensional (3D) reconstruction from the plurality of fluoroscopic images;
   tracking, using a navigation component, a position of a catheter navigated into a luminal network during a navigation phase, wherein the catheter is configured to receive the biopsy tool and to be placed for guiding the biopsy tool to the target;
   presenting a first slice of the first fluoroscopic 3D reconstruction depicting the catheter in relation to the target, wherein the target is visible in the slice of the first fluoroscopic 3D reconstruction;
   receiving a second plurality of fluoroscopic images;
   generating a second fluoroscopic 3D reconstruction from the second plurality of fluoroscopic images;
   defining a first range of images from which a second slice of the second fluoroscopic 3D reconstruction is selected, the first defined range of images corresponding to a first end portion of the second plurality of fluoroscopic images and including less than half but greater than one of the second plurality of fluoroscopic images;
   presenting, on a user interface, an indicator marking each of a beginning and an end of the first defined range of images within the second plurality of fluoroscopic images;
   presenting, on the user interface, the second slice of the second slice of the second fluoroscopic 3D reconstruction depicting the catheter, the second slice selected from the first defined range of images;
   receiving, via the user interface, an indication of a location of a tip of the catheter in the second slice of the second fluoroscopic 3D reconstruction;
   defining a second range of images, the second defined range of images corresponding to a second, opposite end portion of the second plurality of fluoroscopic images and including less than half but greater than one of the second plurality of fluoroscopic images;
   presenting, on the user interface, an indicator marking each of a beginning and an end of the second defined range of images within the second plurality of fluoroscopic images;
   presenting, on the user interface, a third slice of the second fluoroscopic 3D reconstruction depicting a target location, the third slice selected from the second defined range of images;
   receiving, via the user interface, an indication of a location of the target in the third slice of the second fluoroscopic 3D reconstruction; and
   updating a relative position of the target and the catheter in a 3D model of the luminal network.

2. The method of claim 1, further comprising receiving, via the user interface, an indication of a position of the target.

3. The method of claim 1, wherein, after updating of the relative position, the catheter is navigated to the target and a biopsy tool is inserted into the target.

4. The method of claim 1, further comprising receiving, via the user interface, an indication of the location of the target in a fourth slice of the second fluoroscopic 3D reconstruction.

5. The method of claim 4, wherein the first, second, third, and fourth slices of the second fluoroscopic 3D reconstruction are presented on the user interface.

6. The method of claim 5, wherein the third and fourth slices of the second fluoroscopic 3D reconstruction depict images of the target at different relative angles.

7. The method of claim 1, further comprising generating the 3D model of the luminal network from a pre-procedure computed tomography image data set.

8. The method of claim 7, further comprising corresponding, via the navigation component, the position of the catheter to the 3D model of the luminal network.

9. The method of claim 8, further comprising identifying the target in the 3D model of the luminal network.

10. The method of claim 9, wherein tracking, using the navigation component, the position of the catheter navigated into the luminal network includes tracking, using an electromagnetic navigation system, the position of the catheter navigated into the luminal network during the navigation phase.

11. The method of claim 4, further comprising selectively displaying, on the user interface, individual images from the second fluoroscopic 3D reconstruction.

12. The method of claim 11, further comprising displaying, on the user interface, a marker in each image depicting the position of the target.

13. The method of claim 12, further comprising displaying, on the user interface, a scroll bar which upon receiving an input scrolls the images from the second fluoroscopic 3D reconstruction displayed on the user interface, wherein each image includes the marker.

14. The method of claim 13, further comprising automatically generating the marker on each image based on the marking of the target in the third slice.

15. The method of claim 13, further comprising depicting a position of the catheter relative to the target defined by the display marker.

16. The system of claim 13, further comprising depicting a position of the tool extended from the catheter relative to the target defined by the displayed marker.

17. The system of claim 16, further comprising displaying, on the user interface, a next button to confirm that the tool is placed appropriately in the target on images of the second fluoroscopic 3D reconstruction.

18. The system of claim 13, further comprising displaying, on the user input, a second scroll bar which upon receiving an input permits scrolling through a video of the images from the second fluoroscopic 3D reconstruction displayed on the user interface.

19. The system of claim 1, further comprising displaying the indicator marking the beginning and end of the first defined range of images adjacent a thumbnail depicting the second slice of the second fluoroscopic 3D reconstruction, wherein the indicator marking the beginning and end of the first defined range of images and the thumbnail are displayed simultaneously with the second slice of the second fluoroscopic reconstruction.

20. The system of claim 19, further comprising presenting, on the user interface, a fourth slice of the second fluoroscopic 3D reconstruction depicting the catheter, the fourth slice selected from the second defined range of images, wherein the second indicator marking the beginning and end of the second defined range of images is displayed adjacent a second thumbnail depicting the second slice of the second fluoroscopic 3D reconstruction, wherein the second indicator marking the beginning and end of the second defined range of images and the second thumbnail are displayed simultaneously with the fourth slice of the second fluoroscopic 3D reconstruction.

* * * * *